United States Patent [19]

Kajikuri et al.

[11] Patent Number: 5,502,184
[45] Date of Patent: Mar. 26, 1996

[54] PROCESS FOR PRODUCING ε-CAPROLACTAM

[75] Inventors: Hiroshi Kajikuri, Ibaraki; Hideto Tojima, Kyoto; Tomokazu Nakamura, Toyonaka; Masaru Kitamura, Takatsuki, all of Japan

[73] Assignee: Sumitomo Chemical Company, Limited, Osaka, Japan

[21] Appl. No.: 293,169

[22] Filed: Aug. 19, 1994

[30] Foreign Application Priority Data

Aug. 20, 1993 [JP] Japan ..................................... 5-206527

[51] Int. Cl.⁶ ................................................. C07D 201/04
[52] U.S. Cl. ........................... 540/536; 540/535; 540/540
[58] Field of Search ..................................... 540/536, 535, 540/540

[56] References Cited

U.S. PATENT DOCUMENTS

| | | | |
|---|---|---|---|
| 4,563,308 | 1/1986 | Plantema et al. ........................ | 540/540 |
| 4,927,924 | 5/1990 | Bell et al. ................................. | 540/538 |
| 5,032,684 | 7/1991 | Neubauer et al. ....................... | 540/540 |

FOREIGN PATENT DOCUMENTS

| | | | |
|---|---|---|---|
| 0411455 | 7/1991 | European Pat. Off. ............... | 540/540 |
| 1253716 | 9/1969 | Germany .............................. | 540/540 |

OTHER PUBLICATIONS

Romero et al., "Purification of Σ-Caprolactam by Catalytic Hydrogenation. A Statistical Approach", The Canadian Journal of Chemical Engineering, vol. 60, No. 2, Apr. 1982.

Chemical Abstracts, vol. 96, No. 24, 14 Jun. 1982.

*Primary Examiner*—Robert T. Bond
*Attorney, Agent, or Firm*—Cushman Darby & Cushman

[57] ABSTRACT

The invention provides a process for producing high quality ε-caprolactam which comprises allowing crude ε-caprolactam obtained by gas phase Beckmann rearrangement of cyclohexanone oxime to contact with hydrogen at 100°–200° C. in the presence of a hydrogenation catalyst.

13 Claims, No Drawings

PROCESS FOR PRODUCING ε-CAPROLACTAM

FIELD OF THE INVENTION

The present invention relates to a process for producing ε-caprolactam (hereinafter referred to as "lactam") and more particularly, to a process for producing high quality lactam by contacting crude lactam obtained by gas phase Beckmann rearrangement of cyclohexanone oxime (hereinafter referred to as "oxime") with hydrogen in the presence of a hydrogenation catalyst.

BACKGROUND OF THE INVENTION

High quality lactam is used as raw material for polyamide fibers and polyamide resins. It is well known that the lactam is produced in the following manner. That is, oxime is rearranged in a sulfuric acid medium, then neutralized with aqueous ammonia and extracted with an aromatic hydrocarbon solvent such as benzene, followed by removing the solvent by distillation and then subjecting the residue to rectification ("Kogyo Yuki Kagaku (Industrial Organic Chemistry)", page 244 published from Tokyo Kagaku Dojin in 1989).

However, in the case of oxime being rearranged in gas phase using a solid acid in place of sulfuric acid as a catalyst, when the resulting crude lactam is dissolved in water and the solution is mixed with an aromatic solvent such as benzene, lactam cannot be extracted into the aromatic solvent layer probably because the aqueous solution does not contain inorganic materials and the above process which is effective in the case of oxime being rearranged in a sulfuric acid medium cannot be applied to the production of lactam when a solid acid catalyst is used.

When oxime is rearranged in gas phase using a solid acid catalyst and when the resulting crude lactam is subjected to rectification, lactam of satisfactory quality cannot be obtained probably because by-products differ from those in the case of oxime being rearranged in the sulfuric acid medium.

Another effective process for producing high quality lactam comprises treating a crude lactam obtained by Beckmann rearrangement in fuming sulfuric acid with hydrogen at 50°–80° C. using a palladium or nickel supported catalyst. According to this process, when the hydrogen treatment temperature is 130° C., not only sufficient purification effect cannot be obtained, but also quality of lactam is degraded (U.S. Pat. No. 5,032,284).

However, even when crude lactam obtained by gas phase Beckmann rearrangement is subjected to hydrogen treatment at 50°–80° C., no lactam of satisfactory quality can be obtained probably because the by-products differ from those in the case of employing liquid phase rearrangement.

SUMMARY OF THE INVENTION

The inventors have conducted intensive research in an attempt to find an excellent process for producing high quality lactam by gas phase Beckmann rearrangement. As a result, it has been found that a high quality lactam can be obtained by allowing a crude lactam obtained by gas phase Beckmann rearrangement of oxime to contact with hydrogen at a temperature of a high temperature region of 100°–200° C. in the presence of a hydrogenation catalyst.

That is, the present invention provides a process for producing lactam, characterized by allowing crude lactam obtained by gas phase Beckmann rearrangement of oxime to contact with hydrogen at 100°–200° C. in the presence of a hydrogenation catalyst.

DETAILED DESCRIPTION OF THE INVENTION

The present invention will be explained in detail below.

In the present invention, crude lactam obtained by gas phase Beckmann rearrangement of oxime is used. Usually, crude lactam obtained by using solid acid catalysts such as zeolite catalysts U.S. Pat. No. 4,709,024, U.S. Pat. No. 5,212,302), boric acid catalysts (U.S. Pat. No. 4,141,896), silica. alumina catalysts (British Patent No. 831,927) and solid phosphoric acid catalyst (British Patent No. 881,926), is used.

When the crude lactam obtained by the rearrangement is subjected to hydrogenation treatment, the crude lactam can be used as it is or after subjected to pretreatments such as distillation, extraction and adsorption.

Furthermore, the crude lactam per se may be molten, but it may be dissolved in water or organic solvents and in this case, water is preferred as the solvent. The solvent is used in an amount of normally 0.05–50, preferably 0.1–20 times the weight of lactam.

The hydrogenation catalysts used usually contain one or more transition metals of Group VIII such as palladium, platinum, ruthenium and rhodium. Preferred are those which comprise the above transition metals supported on carriers such as active carbon, alumina, silica and titania. More preferred are those which use active carbon as a carrier, and especially preferred are those which comprise active carbon and palladium supported thereon.

The supported catalysts include one which is obtained by dispersing and supporting a metal on the surface of a finely grinded carrier, one which is obtained by dispersing and supporting a metal on the surface of a finely grinded carrier and then molding it, and one which is obtained by molding a fine carrier material and then supporting a metal on the surface of the carrier. Among them, the one which is obtained by dispersing and supporting a metal on the surface of a finely grinded carrier, and the one which is obtained by molding a fine carrier material and then supporting a metal on the surface of the carrier are preferred.

The shape of the catalyst has no special limitation and for example, a catalyst which is molded into pellets or beads can be used.

The amount of the transition metal supported is usually 0.01–20%, preferably 0.01–10%, more preferably 0.1–10% based on the total weight of the catalyst.

The amount of the catalyst based on lactam is normally 0.1 wt % or more in terms of the total weight of the catalyst and $1\times10^{-4}$ wt % or more in terms of the amount of the metal in the case of batch reaction system.

In practicing the present invention, a method which can allow the hydrogenation catalyst and lactam to sufficiently contact with each other is employed. Such method comprises, for example, suspending the hydrogenation catalyst in lactam and stirring the suspension under the hydrogen (batch system) or packing the hydrogenation catalyst in a column and passing lactam and hydrogen therethrough to contact them (continuous passing system).

The amount of hydrogen used for the hydrogenation is usually 0.01 mole or more for 1 mole of lactam.

The hydrogenation treatment is carried out usually at 100°–200° C., preferably at 100°–180° C., and more preferably at 130°–170° C.

The pressure is usually 0.1–10 MPa, preferably 0.1–3 MPa, more preferably 0.2–1 MPa.

The reaction time is usually 0.1–10 hours in the cases of batch method and in some case, the treatment can be repeatedly carried out. In the case of continuous passing method, the contacting time is normally 0.01–5 hours.

Furthermore, the hydrogenation can be carried out in the presence of an acid, whereby quality of lactam obtained can be further improved. As examples of the acid, mention may be made of mineral acids such as sulfuric acid and solid acids such as aluminosilicate, activated clay, niobic acid, heteropoly-acid and cation-exchange resins. Among them, cation-exchange resins are preferred and especially preferred are sulfonic acid type resins of strong acidity and those having a high surface area and a large ion exchange capacity are convenient.

Amount of the cation-exchange resin allowed to be present together is usually 0.1–10 wt %, preferably 0.2–5 wt % based on lactam though it varies depending on the crude lactam to be treated, reaction conditions and ion exchange capacity.

Thus, high quality lactam can be obtained, but it may be further subjected to purification operations such as distillation, extraction and crystallization.

According to the present invention, high quality lactam can be obtained by allowing crude lactam obtained by gas phase Beckmann rearrangement of oxime to contact with hydrogen at a temperature in a high temperature region of 100°–200° C. in the presence of a hydrogenation catalyst.

The present invention is explained in more detail by the following non-limiting examples.

[Evaluation of Quality and Analysis]

(1) Purity was obtained by gas chromatography.

(2) UV transmittance was obtained by measuring transmittance at 290 nm and 315 nm of a solution prepared by dissolving 1.13 g of ε-caprolactam in a distilled water to make up 10 ml.

(3) PM value was obtained in the following steps of ①–②.

① 1.0 Gram of ε-caprolactam was dissolved in a distilled water to prepare 100 ml of solution. To the solution was added 2 ml of 0.01N aqueous potassium permanganate solution and immediately thereafter, stirring was carried out and 250 seconds after addition of the aqueous potassium permanganate solution, absorbance of the solution for a light of 420 nm was measured at 25° C. (temperature of solution).

② Absorbance of distilled water for a light of 420 nm was subtracted from the absorbance of ε-caprolactam measured in ① and the resulting value was multiplied by 100 to obtain PM value.

(4) Amount of volatile base (VB value) was obtained by the following procedure.

5 Grams of sample and 8 ml of 20 % aqueous sodium hydroxide solution were charged in a distillation flask and subjected to steam distillation. The distillate was led to a conical flask containing 5 ml of 0.01N aqueous sulfuric acid solution and the steam distillation was continued until amount of the distillate reached 150 ml.

To the distillate was added a mixed indicator comprising methyl red and methylene blue, and excess sulfuric acid was back titrated with 0.01N aqueous sodium hydroxide solution.

Blank test was conducted in the same manner and amount of volatile base (VB value) was calculated by the following formula.

Amount of volatile base (VB value: in terms of $NH_3$)= $[0.17 \times (B-A) \times f \times 1000]/S$ 0.17: Amount of $NH_3$ (mg) corresponding to 1 ml of 0.01N aqueous sodium hydroxide solution.

f: Factor of 0.01N aqueous sodium hydroxide solution.

B: Consumption amount (ml) of the blank 0.01N aqueous sodium hydroxide solution.

A: Consumption amount (ml) of the sample 0.01N aqueous sodium hydroxide solution.

S: Weight of the sample (mg).

(5) The pH value was obtained by measuring pH of solution prepared by dissolving 5 g of the sample in 20 ml of deionized water adjusted to pH=5.70.

Comparative Example 1

0.375 Gram (0.6 ml) of a zeolite catalyst (U.S. Pat. No. 5,212,302, Si/Al=147,000) was packed in a quartz tube of 1 cm in inner diameter and preheated at 350° C. for 1 hour under nitrogen stream (4.2 liter/hr).

With feeding nitrogen at the same rate, a mixed solution of oxime/methanol of 1/1.8 in weight ratio was fed to the reaction tube at a rate of 8.4 g/hr and the reaction was allowed to proceed for 24 hours. The catalyst layer had a temperature (reaction temperature) of 370° C. The same operation was carried out 30 times in total. The resulting reaction mixtures were collected and methanol was distilled off, followed by distillation to obtain crude lactam.

Purity, UV transmittance and PM value of the resulting crude lactam were measured and the results are shown in Table 1.

Example 1

8 Grams of the crude lactam obtained in Comparative Example 1 was dissolved in 20 g of water and the solution was charged in a 100 ml stainless steel autoclave. Furthermore, 0.08 g of a hydrogenation catalyst (powdery 5 % Pd/C) was charged in the autoclave and the autoclave was closed. Then, the air in the autoclave was replaced with hydrogen (0.4 MPa). Then, the autoclave was dipped in an oil bath of 100° C. and the content was stirred for 1 hour. In this case, the inner pressure was 0.5 MPa. The treated solution was filtrated to remove the hydrogenation catalyst and then, water in the filtrate was distilled off under reduced pressure to obtain lactam. Purity, UV transmittance and PM value of the resulting crude lactam were measured and the results are shown in Table 1.

Example 2

The hydrogenation treatment was effected in the same manner as in Example 1 except that temperature of the oil bath was 150° C. Inner pressure of the autoclave at treatment was 0.95 MPa. Purity, UV transmittance and PM value of the resulting crude lactam were measured and the results are shown in Table 1.

Comparative Example 2

The hydrogenation treatment was effected in the same manner as in Example 1 except that temperature of the oil bath was 50° C. Inner pressure of the autoclave at the treatment was 0.4 MPa. Purity, UV transmittance and PM value of the resulting crude lactam were measured and the results are shown in Table 1.

TABLE 1

| | Purity (%) | UV transmittance (%) | | PM Value |
|---|---|---|---|---|
| | | 290 nm | 315 nm | |
| Comparative Example 1 | 99.61 | 0.3 | 0.3 | 232.0 |
| Example 1 | 99.87 | 0.3 | 0.5 | 46.0 |
| Example 2 | 99.88 | 2.4 | 7.9 | 19.2 |
| Comparative Example 2 | 99.85 | 0.3 | 0.3 | 76.0 |

Example 3

The hydrogenation treatment was effected in the same manner as in Example 1 except that the hydrogenation catalyst was used in an amount of 1.2 g, thereby to obtain lactam. Inner pressure of the autoclave at the treatment was 0.5 MPa. Purity, UV transmittance and PM value of the resulting crude lactam were measured and the results are shown in Table 2.

TABLE 2

| | Purity (%) | UV transmittance (%) | | PM Value |
|---|---|---|---|---|
| | | 290 nm | 315 nm | |
| Comparative Example 1 | 99.61 | 0.3 | 0.3 | 232.0 |
| Example 3 | 99.98 | 93.7 | 95.7 | 1.0 |

Comparative Example 3

A solution prepared by dissolving 975 g of the crude lactam obtained in Comparative Example 1 in 975 g of water and 2925 ml of cyclohexane were charged in a 5 liter separating funnel and shaken for 30 minutes at room temperature and then left to stand for 15 minutes. The aqueous layer was separated and charged in a 5 liter separating funnel and shaken. Furthermore, 2,925 ml of cyclohexane was added thereto and the content was shaken at room temperature for 30 minutes and left to stand for 15 minutes, and the aqueous layer was separated. Further, this operation was repeated 8 times and water was distilled off from the resulting aqueous layer under reduced pressure to obtain 790 g of extracted crude lactam. Purity, UV transmittance and PM value of the resulting crude lactam were measured and the results are shown in Table 3.

Example 4

The hydrogenation treatment was effected in the same manner as in Example 1 except that 8 g of the extracted crude lactam obtained in Comparative Example 3 was used in place of the crude lactam obtained in Comparative Example 1. Inner pressure of the autoclave at the treatment was 0.5 MPa. Purity, UV transmittance and PM value of the resulting crude lactam were measured and the results are shown in Table 3.

Examples 5–9

The hydrogenation treatment was effected in the same manner as in Example 4 except that the hydrogenation catalyst as shown in Table 3 was used in an amount as shown in Table 3. Inner pressure of the autoclave at the treatment was 0.5 MPa. Purity, UV transmittance and PM value of the resulting crude lactam were measured and the results are shown in Table 3.

TABLE 3

| | Hydrogenation catalyst | | Purity (%) | UV transmittance (%) | | PM Value |
|---|---|---|---|---|---|---|
| | Kind | Amount[1] | | 290 nm | 315 nm | |
| Comparative Example 3 | — | — | 99.75 | 7.9 | 16.1 | 229.0 |
| Example 4 | 5% Pd/C | 0.01 | 99.89 | 21.4 | 39.4 | 36.4 |
| Example 5 | 5% Pd/C | 0.15 | 99.98 | 94.9 | 96.6 | 1.3 |
| Example 6 | 5% Ru/C | 0.15 | 99.91 | 90.8 | 93.3 | 2.2 |
| Example 7 | 2.5% Pd.2.5% Ru/Al$_2$O$_3$ | 0.15 | 99.93 | 73.8 | 79.0 | 4.2 |
| Example 8 | 5% Ru/Al$_2$O$_3$ | 0.15 | 99.92 | 67.3 | 71.7 | 4.1 |
| Example 9 | 5% Pt/C | 0.15 | 99.94 | 38.0 | 41.4 | 1.1 |

[1] Weight ratio to the extracted crude lactam.

Example 10

The hydrogenation treatment was effected in the same manner as in Example 4 except that 0.08 g of powdery 1% Pd/C was used as the hydrogenation catalyst, temperature of the oil bath was 150° C. and amount of water was 80 g. Inner pressure of the autoclave at the treatment was 0.8 MPa. Purity, UV transmittance and PM value of the resulting crude lactam were measured and the results are shown in Table 4.

TABLE 4

| | Purity (%) | UV transmittance (%) | | PM Value |
|---|---|---|---|---|
| | | 290 nm | 315 nm | |
| Comparative Example 3 | 99.75 | 7.9 | 16.1 | 229.0 |
| Example 10 | 99.90 | 61.9 | 75.1 | 13.7 |

Example 11

1.27 Grams of a hydrogenation catalyst (0.3–0.7 mmφ, 1% Pd/C) was packed in a stainless steel column (inner diameter: 9 mmφ) and heated to 145° C. with feeding hydrogen gas (18 liters/hr). After heating, an aqueous solution of the extracted crude lactam obtained in Comparative Example 3 (lactam concentration: 20% by weight) was further fed to the column at a rate of 15 g/hr with feeding hydrogen gas at 145° C. In this case, the pressure in the column was kept at 0.6 MPa. The treated solution was taken for 2 hours after lapse of 50 minutes from starting of feeding of the solution. Water was distilled off from the resulting treated solution under reduced pressure to obtain lactam. Purity, UV transmittance and PM value of the resulting lactam were measured and the results are shown in Table 5.

TABLE 5

| | Purity (%) | UV transmittance (%) | | PM Value |
|---|---|---|---|---|
| | | 290 nm | 315 nm | |
| Comparative Example 3 | 99.75 | 7.9 | 16.1 | 229.0 |
| Example 11 | 99.84 | 39.3 | 53.2 | 26.4 |

Example 12

The hydrogenation treatment was effected in the same manner as in Example 2 except that amount of the hydrogenation catalyst was 0.16 g and amount of water was 40 g. After the hydrogenation catalyst was removed by filtration, water was distilled off under reduced pressure to obtain lactam. Purity, UV transmittance and PM value of the lactam were measured and the results are shown in Table 6.

Example 13

The hydrogenation treatment was effected under the same conditions as in Example 12 except that the hydrogenation treatment was effected on a scale of 5 times, thereby to obtain lactam. This lactam was subjected to vacuum distillation under the conditions of 5 mmHg and a refluxing ratio of 10 using a distillation column (real plate efficiency: 40) to obtain distilled lactam. Purity, UV transmittance and PM value of the distilled lactam were measured and the results are shown in Table 6.

Comparative Example 4

40 Grams of the crude lactam obtained in Comparative Example 1 was subjected to vacuum distillation under the same conditions as in Example 13 without subjecting to hydrogenation treatment, thereby to obtain distilled lactam. Purity, UV transmittance and PM value of the resulting distilled lactam were measured and the results are shown in Table 6.

TABLE 6

| | Purity (%) | UV transmittance (%) | | PM Value |
|---|---|---|---|---|
| | | 290 nm | 315 nm | |
| Comparative Example 1 | 99.61 | 0.3 | 0.3 | 232.0 |
| Example 12 | 99.93 | 36.9 | 56.3 | 18.4 |
| Example 13 | 99.99 | 97.1 | 98.0 | 2.2 |
| Comparative Example 4 | 99.90 | 0.3 | 0.5 | 140.0 |

Example 14

40 Grams of the extracted crude lactam obtained in Comparative Example 3, 100 g of water and 0.4 g of 1% Pd-C (catalyst comprising Pd supported on the surface of carbon beads) were charged in a 250 ml autoclave and were stirred at 150° C. for 1 hour at 0.95 MPa after the inner atmosphere was replaced with hydrogen.

The resulting lactam was distilled in the same manner as in Example 13 to obtain distilled lactam. Purity was 99.98%, UV transmittance was 95.1 (290 nm), 96.5 (315 nm), and PM value was 3.1.

Example 15

50 Grams of the extracted crude lactam obtained in Comparative Example 3, 125 g of water, 5 g of 1% Pd-$Al_2O_3$ and 0.8 of a cation exchange resin (Duolite C-26-H) were charged in a 550 ml autoclave and were stirred at 100° C. for 1 hour at 0.5 MPa after the inner atmosphere was replaced with hydrogen.

The resulting lactam was distilled in the same manner as in Example 13 to obtain distilled lactam. The results of analysis are shown in Table 7.

Comparative Example 5

The extracted crude lactam obtained in Comparative Example 3 was distilled in the same manner as in Example 13 to obtain distilled lactam. The results of analysis are shown in Table 7.

TABLE 7

| | Purity (%) | UV transmittance (%) | | PM Value | VB Value | pH Value |
|---|---|---|---|---|---|---|
| | | 290 nm | 315 nm | | | |
| Example 15 | 99.99 | 98.8 | 99.2 | 0.6 | 1.7 | 6.02 |
| Comparative Example 5 | 99.98 | 94.2 | 97.4 | 20 | 9.1 | 7.92 |

We claim:
1. A process for producing ε-caprolactam which consists essentially of allowing crude ε-caprolactam obtained by gas phase Beckmann rearrangement of cyclohexanone oxime to contact hydrogen at 100°–200° C. in the presence of a hydrogenation catalyst.

2. A process according to claim 1 wherein the crude ε-caprolactam is obtained using a solid acid catalyst selected from zeolite catalysts, phosphoric acid catalysts, silica-alumina catalysts and solid phosphoric acid catalysts.

3. A process according to claim 1 wherein a catalyst comprising a transition metal of Group VIII supported on a carrier is used as the hydrogenation catalyst.

4. A process according to claim 3 wherein the transition metal is at least one member selected from palladium, platinum, ruthenium and rhodium.

5. A process according to claim 3 wherein the carrier is at least one member selected from active carbon, alumina, silica and titania.

6. A process according to claim 3 wherein the transition metal is palladium and the carrier is active carbon.

7. A process according to claim 3 wherein amount of the transition metal supported is 0.01–20% based on the total weight of the catalyst.

8. A process according to claim 1 which is carried out in the presence of an acid.

9. A process according to claim 8 wherein the acid is at least one acid selected from aluminosilicate, activated clay, niobic acid, hetero-poly acid and cation exchange resin.

10. A process according to claim 8 wherein amount of the acid is 0.1–10% by weight based on the crude lactam.

11. A process according to claim 1 wherein reaction temperature is 130°–170° C.

12. A process according to claim 1 wherein reaction pressure is 0.1–10 MPa.

13. A process for producing ε-caprolactam which consists of allowing a crude ε-caprolactam obtained by gas phase Beckmann rearrangement of cyclohexanone oxime to contact hydrogen at 100°–200° C. in the presence of a hydrogenation catalyst.

* * * * *